United States Patent [19]
von Werner

[11] Patent Number: 5,344,580
[45] Date of Patent: Sep. 6, 1994

[54] OLIGOMERS OF FLUORINATED OLEFINS

[75] Inventor: Konrad von Werner, Wald/Alz, Fed. Rep. of Germany

[73] Assignee: Hoechst Aktiengesellschaft, Burgkirchen

[21] Appl. No.: 983,691

[22] Filed: Dec. 1, 1992

[30] Foreign Application Priority Data

Dec. 3, 1991 [DE] Fed. Rep. of Germany ....... 4139765

[51] Int. Cl.$^5$ ................ C10M 147/00; C10M 131/00
[52] U.S. Cl. ........................................ 252/54; 252/58; 568/683; 568/685; 570/126; 570/136; 106/270; 106/271
[58] Field of Search ................ 568/683, 685; 570/126, 570/136; 252/54, 58

[56] References Cited

U.S. PATENT DOCUMENTS

| | | | |
|---|---|---|---|
| 3,180,895 | 4/1965 | Harris, Jr. et al. ................. | 568/685 |
| 3,240,825 | 3/1966 | Hauptschein et al. ................. | 252/58 |
| 3,665,041 | 5/1972 | Sianesi et al. ......................... | 252/54 |
| 4,606,832 | 8/1986 | Hisamoto et al. ..................... | 252/8 |
| 4,668,749 | 5/1987 | Graun et al. .......................... | 526/245 |
| 4,673,712 | 6/1987 | Fukui et al. ........................... | 526/253 |
| 4,987,267 | 1/1991 | Takaoka et al. ....................... | 568/615 |
| 5,114,482 | 5/1992 | Hertel ..................................... | 252/58 |

FOREIGN PATENT DOCUMENTS 0399817 11/1990 European Pat. Off. .
4000661 7/1990 Fed. Rep. of Germany .

Primary Examiner—Ellen M. McAvoy

[57] ABSTRACT

Oligomers of compounds of the formula $$X\text{—}(CF_2)_a\text{—}O_b\text{—}(CH_2)_c\text{—}CH=CH_2 \qquad (1)$$

and co-oligomers of compounds of the formula (1) together with compounds of the formula $$X\text{—}(CX_2)_d\text{—}O_b\text{—}(CX_2)_c\text{—}CX=CX_2 \qquad (2)$$

in which X is hydrogen or fluorine, a is a number from 2 to 16, b and c are, independently of one another, 0 or 1, and d is a number from 0 to 6, with a mean degree of oligomerization of 2 to 4, are obtained by heating a solution of the monomers in a hydrocarbon together with a free radical-forming catalyst to 135° to 180° C. The oligomers are lubricating agents and lubricants.

16 Claims, No Drawings

OLIGOMERS OF FLUORINATED OLEFINS

DESCRIPTION

The invention relates to oligomers of compounds of the formula $$X-(CF_2)_a-O_b-(CH_2)_c-CH=CH_2 \quad (1)$$

and co-oligomers of compounds of the formula (1) with compounds of the formula $$X-(CX_2)_d-O_b-(CX_2)_c-CX=CX_2 \quad (2)$$

In these formulae: X is hydrogen or fluorine, a is a number from 2 to 16, b and c are, independently of one another, 0 or 1, and d is a number from 0 to 6.

Oligomers in which X is fluorine, a is a number from 4 to 12, and b and c are both zero are preferred.

The mean degree of oligomerization of these compounds is 2 to 4.

The oligomers according to the invention are obtained by heating a solution of at least one compound of the formula (1), optionally with at least one compound of the formula (2), in a hydrocarbon to a temperature of 135 to 180° C. together with a free radical-forming catalyst.

Preferred solvents are saturated hydrocarbons such as alkanes with 5 to 12 carbon atoms and readily accessible cycloalkanes such as cyclohexane.

Preferred free radical-forming catalysts are peroxides, especially dialkyl peroxides. Symmetrical dialkyl peroxides having in each alkyl 6 to 16 carbon atoms are particularly preferred.

The preferred reaction temperature is in the range from 140° to 160° C.

Preferred starting materials of the formula (1) are perfluoroalkylethylenes having a perfluoroalkyl radical with 4 to 12 carbon atoms, and the corresponding compounds with a terminal hydrogen atom on the fluoroalkane chain. Furthermore, the corresponding vinyl and allyl ethers are preferred.

Preferred comonomers of the formula (2) are optionally fluorinated mono-ethylenically unsaturated hydrocarbons with 2 to 6 carbon atoms as well as optionally fluorinated alkyl vinyl and alkyl allyl ethers. Ethylene, 1-octene, 1,1,2,2-tetrafluoroethyl 3',3'-difluoroallyl ether as well as hexafluoropropene may be mentioned.

The oligomers and co-oligomers according to the invention are highly hydrophobic and relatively oleophobic, but are fluorophilic, and are therefore suitable for use as lubricants on surfaces, particularly of plastics, metal or glass. The products can for example easily be applied by simply rubbing them on polyethylene sheets. Upon the slightest shaking water runs in the form of almost spherical droplets over the surface of sheets treated in this way, whereas water clearly adheres to untreated sheets. If the compounds according to the invention are applied to the undersides of polyethylene skis optionally treated with graphite, this produces a very good running behavior on wet snow. The compounds may be applied in a conventional manner, for example as ski wax. The compounds according to the invention can also be processed, by the pressure sintering technique, together with polyethylene to form a material from which ski coatings with a high degree of slip can be prepared.

Since the oligomers according to the invention are miscible with perfluoroalkanes, fluoroalkane waxes that are otherwise difficult to apply to surfaces can be applied with their help.

Extremely thin oligomer films greatly reduce glass-on-glass friction. Metal-metal friction too is greatly reduced. An addition of polytetrafluoroethylene micropowder produces a further improvement.

The compounds according to the invention are thus outstandingly suitable for coatings of a very wide range of surfaces, the friction being greatly reduced on surfaces coated in this way.

The invention is described in more detail in the following examples. The molecular weights were determined with a vapor pressure osmometer supplied by Knauer.

EXAMPLE 1

An electrically heated rocking autoclave of 4.5 l capacity is charged with a solution of 1730 g (5.0 mol) of $C_6F_{13}CH=CH_2$ and 51.2 g (0.35 mol) of di-tert-butyl peroxide in 2.0 l of n-hexane. The autoclave is flushed for 10 minutes with a gentle stream of $N_2$, the nitrogen pressure in the autoclave is then raised to 10 bar $N_2$ for a pressure test, and the pressure is slowly released. The autoclave is then heated to 150° C. over 1.5 hours while shaking, and is shaken for 5 hours at this temperature. After cooling to 30° C. (external cooling by blowing with cold air) the autoclave is emptied. A 2-phase mixture is obtained, the upper phase composed mainly of hexane. The solvent is removed in a rotary evaporator. The remaining crude product is suction-filtered under a slight vacuum using a paper filter, in order to remove minor mechanical impurities. The filtrate is distilled with a Vigreux column. A total of 133 g of product distill off at a head temperature of between 25° and 105° C. under 20 mbar. The average molecular weight $\overline{M}$ is 562, i.e. the distillate contains about 60% of dimers. 1593 g of an almost colorless oil are obtained as residue (92.1% yield). The average molar mass is 1070, which is slightly above the molar mass of the $C_6F_{13}CH=CH_2$-trimer (1038).

The oligomeric product is extremely resistant to hot sodium hydroxide. After stirring for 3 hours under reflux with 20% strength NaOH (with and without phase-transfer catalyst), only traces of fluoride were found in the aqueous phase.

EXAMPLE 2

The same procedure as in Example 1 is adopted, except that cyclohexane is used as solvent. A comparable product is obtained in 91% yield.

EXAMPLES 3 TO 10

The preparation of further oligomers is described in the following Table 1, and the production of co-oligomers is described in Table 2.

Examples 7 to 10 were carried out using in each case 100 ml of hexane as solvent.

TABLE 1

| Example | Alkene type | g | mol | DTBO[a)] g | mol % | n-Hexane ml | Temperature °C. | Duration h | Yield g | Features of the product |
|---|---|---|---|---|---|---|---|---|---|---|
| 3 | $C_8F_{17}CH=CH_2$ | 133.8 | 0.3 | 3.07 | 7 | 120 | 150 | 5 | 108.0 | thick oil |

TABLE 1-continued

| Example | Alkene type | g | mol | DTBO[a] g | mol % | n-Hexane ml | Temperature °C. | Duration h | Yield g | Features of the product |
|---|---|---|---|---|---|---|---|---|---|---|
| 4 | $R_FCH=CH_2$[b] | 119.9 | 0.25 | 2.56 | 7 | 100 | 150 | 5 | 115.3 | partially solid[c] |
| 5 | $R_FCH=CH_2$[b] | 1438.5 | 3.0 | 30.7 | 7 | 1200 | 150 | 5 | 1325 | partially solid[c] |
| 6 | $C_8F_{17}CH_2CH=CH_2$ | 115 | 0.25 | 2.56 | 7 | 100 | 150 | 5 | 113.0 | yellowish oil |

[a]Di-tert-butyl peroxide
[b]Technical product: $R_F$ = 4.3% of $C_6F_{13}$, 44.0% of $C_8F_{17}$, 39.1% of $C_{10}F_{21}$, 3.4% of $C_{12}F_{25}$ and longer-chain compounds, remainder impurities such as $R_FH$.
[c]Homogeneous liquid above 40° C. DSC measurements under autogenous pressure did not show any significant decomposition up to 400° C.

TABLE 2

| Example | Alkene I Type | g | mol | Alkene II Type | g | mol | DTBO[a] g | Temperature °C. | Duration h | Yield g |
|---|---|---|---|---|---|---|---|---|---|---|
| 7 | $C_6F_{13}CH=CH_2$ | 69.2 | 0.2 | $C_6H_{13}CH=CH_2$ | 22.4 | 0.2 | 2.34 | 150 | 5 | 82.9 |
| 8 | $C_6F_{13}CH=CH_2$ | 86.5 | 0.25 | $CH_2=CH_2$ | 14 | 0.5 | 2.56 | 150 | 5 | 97.9 |
| 9 | $C_6F_{13}CH=CH_2$ | 51.9 | 0.15 | $CH_2=CHCH_2OCF_2CF_2H$ | 15.8 | 0.1 | 2.56 | 150 | 5 | 68.0 |
| 10 | $C_6F_{13}CH=CH_2$ | 86.5 | 0.25 | $CF_2=CF-CF_3$ | 37.5 | 0.25 | 2.56 | 150 | 5 | 80.6[b] |

[a]Di-tert-butyl peroxide
[b]Hexafluoropropene proportion: 27.0 mol %

EXAMPLE 11

A mixture of 3.2 l of a higher alkane mixture (SHELLSOL 145/160) of boiling point range 145° to 160° C., 4088 g (about 8 mol) of perfluoroalkylethylene and, dissolved in the latter, 82 g (0.56 mol) of di-tert-butyl peroxide is aspirated into an evacuated 10 l capacity stirred autoclave. The perfluoroalkylethylene had the following composition (as determined by gas chromatography):

| $C_nF_{2n+1}-CH=CH_2$ | 98% |
|---|---|
| n = 8 | 1.2% |
| n = 10 | 67.5% |
| n = 12 | 24.8% |
| n = 14 | 4.1% |
| n ≧ 16 | 0.4% |
| $C_nF_{2n+1}-H$: | 0.3% |
| other impurities | 1.7% |
| Iodine content: | 390 ppm |

The residual vacuum is filled with nitrogen and the autoclave is flushed with nitrogen at a pressure of 5 bar. The pressure in the autoclave is released, the autoclave is closed and then heated to 150° C. within 1.5 hours and the contents are stirred for 5 hours, a maximum pressure of 6 bar being measured. The autoclave is then allowed to cool to about 80° C. and is emptied through a dip tube. The liquid, two-phase reaction product is distilled up to a bottom temperature of 150° C. under 20 mbar. The solvent that passes over contains only very small amounts of fluorinated components and can be used without further purification for another run. The liquid distillation residue (4170 g) solidifies to an easily grindable product, which is still free-flowing after prolonged storage. The melting range is 70° to 80° C.

If a perfluoroalkylethylene containing lower boiling fractions is used, solidifying products with a lower melting range are obtained; for example, when using $C_nF_{2n+1}-CH=CH_2$

| n = 6 | 30.3% | n = 12 | 16.4% |
|---|---|---|---|
| n = 8 | 4.1% | n = 14 | 4.7% |
| n = 10 | 39.9% | n ≧ 16 | 1.6% |
| iodine content: 200 ppm | | | | a product is obtained having a melting range of 40° to 60° C.

EXAMPLE 12

The oligomer according to Example 5 is applied by spincasting from a 1,1,2-trifluorotrichloroethane (•Frigen 113) solution to a carefully cleaned glass plate. After evaporating off the solvent the plate is heated to 40° C. in order to orient the surface film. A dispersive surface energy of only 9 mN/m is calculated from the contact angles θ measured by immersion with n-dodecane and n-hexadecane (according to W. A. Zisman "Contact angle, wettability, and adhesion", Adv. in Chemistry Series, No. 43, Am. Chem. Soc., Washington DC, 1964).

EXAMPLE 13

5000 g of high molecular weight, microgranular polyethylene (•Hostalen GM 7250, Hoechst AG), 1250 g of amorphous carbon (acetylene soot) and 100 g of the perfluoroalkylethylene oligomer according to Example 5 are premixed in batches. The mixture is homogenized in a planetary mixer at a maximum temperature of 70° C. and is then isostatically compressed and sintered into a cylinder in a heated mold while gradually raising the temperature to 200° C. and under a maximum pressure of 200 bar. After cooling, a 1.5 mm thick, almost black sliced sheet is produced from the molding obtained as described above. This sheet is polished to produce a smooth, crack-free surface, as is required for a top-quality coating for racing skis.

Compared to a sliced sheet produced in the same way but without addition of the oligomer, the sheet according to the invention is considerably more water-repellent. Investigations by scanning electron microscopy and ESCA (electron spectroscopy for chemical analysis) show that the oligomer accumulates in particular in the surface regions composed of amorphous polyethylene.

EXAMPLE 14

0.5 % by weight of the oligomer according to the invention is mixed with high molecular weight polyethylene (Hostalen GM 5010 T2) and extruded in an extruder to give tubes having a diameter of 32 mm and a wall thickness of 3 mm. With a screw speed of 80 r.p.m. and a melt temperature in the center of 223±1° C. and an external melt temperature of 211±2° C., the melt pressure was 120 bar.

With a control batch without addition of oligomer, a melt pressure of 135 bar was produced.

Compared to the tube obtained without addition of oligomer, the tubes extruded with addition of oligomer had a much higher gloss, and a viscous oil when flowing through the tube adhered very much less strongly to the tube wall.

The following oligomers were used:

Experiment 1: Product according to Example 5

Experiment 2: Product according to Example 11, melting range 40° to 60° C.

Experiment 3: Product according to Example 11, melting range 70° to 90° C.

I claim:

1. An oligomer of compounds of the formula $$X-(CF_2)_a-O_b-(CH_2)_c-CH=CH_2 \quad (1)$$

and co-oligomers of compounds of the formula (1) together with compounds of the formula $$X-(CX_2)_d-O_b-(CX_2)_c-CX=CX_2 \quad (2)$$

in which X is hydrogen or fluorine, a is a number from 2 to 16, b and c are, independently of one another, 0 or 1, and d is a number from 0 to 6, with a mean degree of oligomerization of 2 to 4.

2. An oligomer of compounds of the formula (1) as claimed in claim 1, in which X is fluorine, a is a number from 4 to 12, and b and c are zero.

3. A process for preparing an oligomer or co-oligomer with a mean degree of oligomerization of 2 to 4, which comprises:

heating a solution of at least one compound of the formula (1)

$$X-(CF_2)_a-O_b-(CH_2)_c-CH=CH_2 \quad (1),$$

or a mixture thereof with at least one compound of the formula (2)

$X-(CX_2)_d-O_b-(CX_2)_c-CX=CX_2$ in which X is hydrogen or fluorine, a is a number from 2 to 16, b and c are, independently of one another, 0 or 1, and d is a number from 0 to 6, in a hydrocarbon to a temperature of 135° to 180° C. together with a free radical-forming catalyst, and recovering a said oligomer or co-oligomer having a mean degree of oligomerization of 2 to 4.

4. A grease or lubricant composition, comprising a hydrophobic grease or lubricant and an oligomer or co-oligomer as claimed in claim 1.

5. A lubricant composition for the underside of skis, comprising a ski wax and an oligomer or cooligomer as claimed in claim 1.

6. A wax composition comprising a fluoroalkane wax and an oligomer or co-oligomer as claimed in claim 1.

7. A ski coating, consisting essentially of polyethylene and an oligomer or co-oligomer as claimed in claim 1.

8. A plastic, metal, or glass substrate coated with an oligomer or co-oligomer as claimed in claim 1.

9. A plastic ski coated on its underside with an oligomer or co-oligomer as claimed in claim 1.

10. A plastic ski as claimed in claim 9, wherein the ski comprises polyethylene plastic.

11. A metal or glass device comprising metal or glass parts, wherein the metal-metal friction or the glass-glass friction is reduced with a film on metal or glass surfaces, said film comprising an oligomer or co-oligomer as claimed in claim 1.

12. A metal or glass device as claimed in claim 11, wherein the film comprises polytetrafluoroethylene micropowder in addition to said oligomer or co-oligomer.

13. A method of lubricating an article, comprising: applying to the surface of the article or including in the composition from which the article is made an oligomer or co-oligomer of claim 1.

14. A method as claimed in claim 13, wherein said article comprises glass, metal, or plastic.

15. A method as claimed in claim 14, wherein said plastic is polyethylene.

16. A method as claimed in claim 13, wherein the article is a ski, and the surface of the article is the underside of the ski.

* * * * *